US011192100B2

(12) United States Patent
McCord et al.

(10) Patent No.: US 11,192,100 B2
(45) Date of Patent: Dec. 7, 2021

(54) MULTI-FACTOR URINE TEST SYSTEM THAT ADJUSTS FOR LIGHTING AND TIMING

(71) Applicant: BLOOM HEALTH, INC., San Diego, CA (US)

(72) Inventors: Matthew McCord, San Diego, CA (US); Jon Carder, San Diego, CA (US); Jesus Gonzalez, San Diego, CA (US); Sergio Alvarez, San Diego, CA (US)

(73) Assignee: VESSEL HEALTH, INC., San Diego, CA (US)

( * ) Notice: Subject to any disclaimer, the term of this patent is extended or adjusted under 35 U.S.C. 154(b) by 0 days.

(21) Appl. No.: 16/828,967

(22) Filed: Mar. 25, 2020

(65) Prior Publication Data

US 2021/0299651 A1    Sep. 30, 2021

(51) Int. Cl.
| | |
|---|---|
| *B01L 3/00* | (2006.01) |
| *G01N 21/78* | (2006.01) |
| *A61B 10/00* | (2006.01) |
| *A61B 5/20* | (2006.01) |
| *G01J 3/50* | (2006.01) |

(52) U.S. Cl.
CPC ............. *B01L 3/502* (2013.01); *A61B 5/207* (2013.01); *A61B 10/007* (2013.01); *G01J 3/50* (2013.01); *G01N 21/78* (2013.01); *B01L 2300/025* (2013.01); *B01L 2300/0663* (2013.01);
(Continued)

(58) Field of Classification Search
CPC ............. B01L 3/502; B01L 2300/0663; B01L 2300/025; B01L 2300/0861; B01L 2300/0816; A61B 10/007; A61B 5/207; G01J 3/50; G01N 21/78
See application file for complete search history.

(56) References Cited

U.S. PATENT DOCUMENTS 5,408,535 A  *  4/1995  Howard, III  .......  G01N 21/8483
                                                         382/128
8,655,009 B2     2/2014  Chen et al.
(Continued)

FOREIGN PATENT DOCUMENTS

| EP | 2916117 A1 | 9/2015 |
|---|---|---|
| WO | 2015134820 A1 | 9/2015 |

*Primary Examiner* — Samuel P Siefke
(74) *Attorney, Agent, or Firm* — Arc IP Law, PC; Joseph J. Mayo

(57) ABSTRACT

System that enables urine testing in a home environment. A user may apply a urine sample to a card containing multiple tests, and capture an image of the card using a phone; an analysis system executing on the phone or in the cloud may analyze the image and determine test results. The test card and analysis system may compensate for variability in lighting conditions and time of exposure to the urine sample, which are difficult to control in a home environment. The test card may contain fiducial markers of known colors; the analysis system may adjust colors in the captured image based on appearance of these markers. Color adjustments may also compensate for nonuniform lighting across the card. The card may also contain time indicators that change appearance over time after urine is applied, and the analysis system may use these indicators to calculate the time of exposure.

25 Claims, 10 Drawing Sheets
(8 of 10 Drawing Sheet(s) Filed in Color)

(52) U.S. Cl.
CPC .............. *B01L 2300/0816* (2013.01); *B01L 2300/0861* (2013.01)

(56) References Cited

U.S. PATENT DOCUMENTS

| | | |
|---|---|---|
| 8,983,181 B2 | 3/2015 | Wachtell et al. |
| 9,240,039 B2 * | 1/2016 | Cong .................. G01N 33/558 |
| 9,285,323 B2 | 3/2016 | Burg et al. |
| 9,311,520 B2 | 4/2016 | Burg et al. |
| 9,383,244 B2 | 7/2016 | Bishop et al. |
| 9,528,941 B2 | 12/2016 | Burg et al. |
| 9,863,811 B2 | 1/2018 | Burg |
| 9,972,077 B2 | 5/2018 | Adiri et al. |
| 10,068,329 B2 | 9/2018 | Adiri et al. |
| 2011/0311370 A1 | 12/2011 | Sloss et al. |
| 2012/0106811 A1 * | 5/2012 | Chen .................. A61B 10/007 382/128 |
| 2013/0267032 A1 * | 10/2013 | Tsai .................. G01N 21/8483 436/95 |
| 2014/0119947 A1 | 5/2014 | Bishop et al. |
| 2015/0055134 A1 * | 2/2015 | Papautsky ............ G01N 21/278 356/408 |
| 2015/0056687 A1 * | 2/2015 | Tyrrell .................. B01L 3/5023 435/287.2 |
| 2015/0160245 A1 * | 6/2015 | Lieberman ........... G01N 33/523 506/12 |
| 2015/0211987 A1 | 7/2015 | Burg et al. |
| 2015/0308961 A1 * | 10/2015 | Burg ...................... G01N 21/78 382/165 |
| 2016/0048739 A1 * | 2/2016 | Burg ...................... H04N 9/735 382/128 |
| 2017/0098137 A1 | 4/2017 | Burg et al. |
| 2018/0017459 A1 | 1/2018 | Banta |

\* cited by examiner

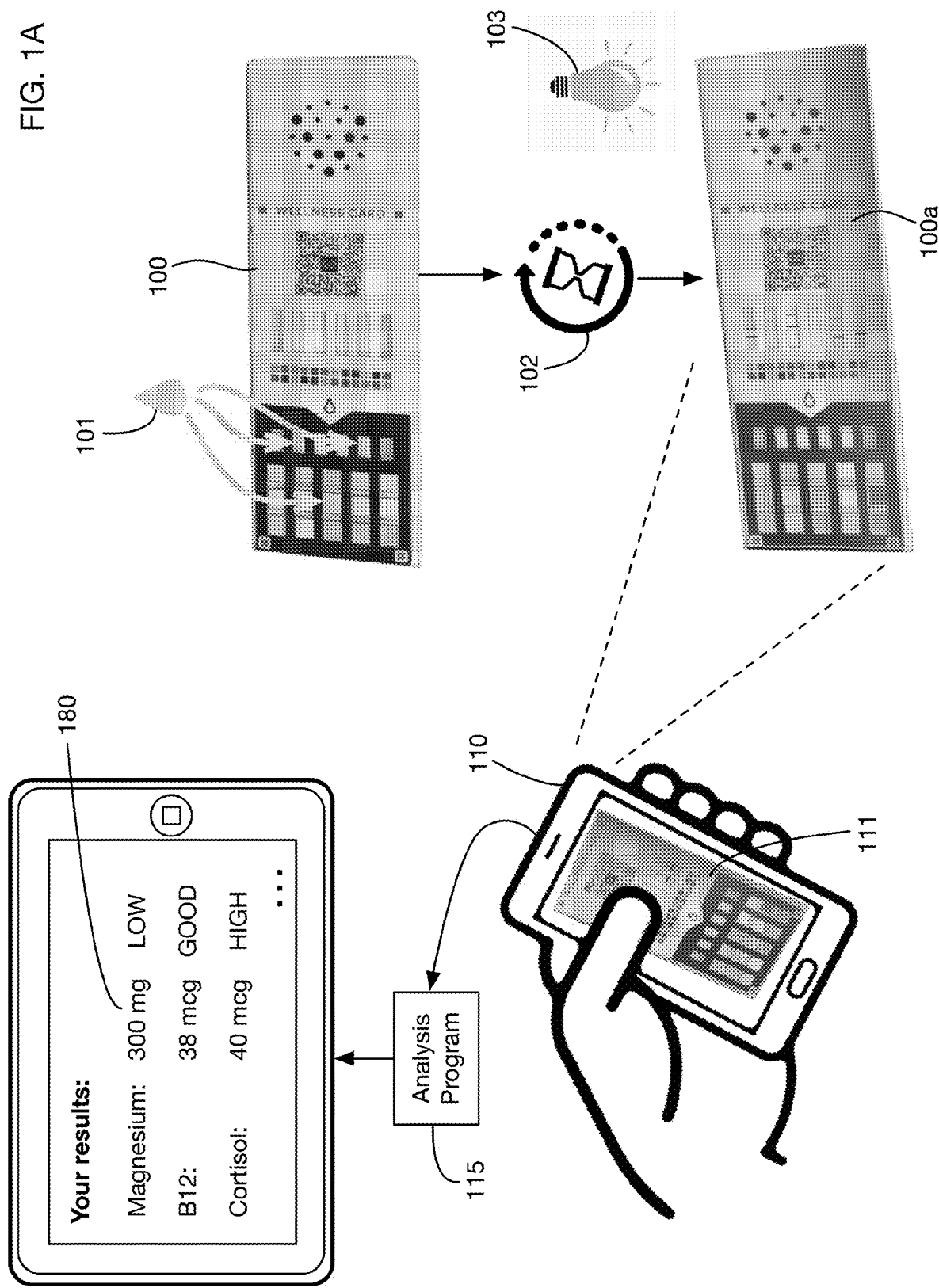

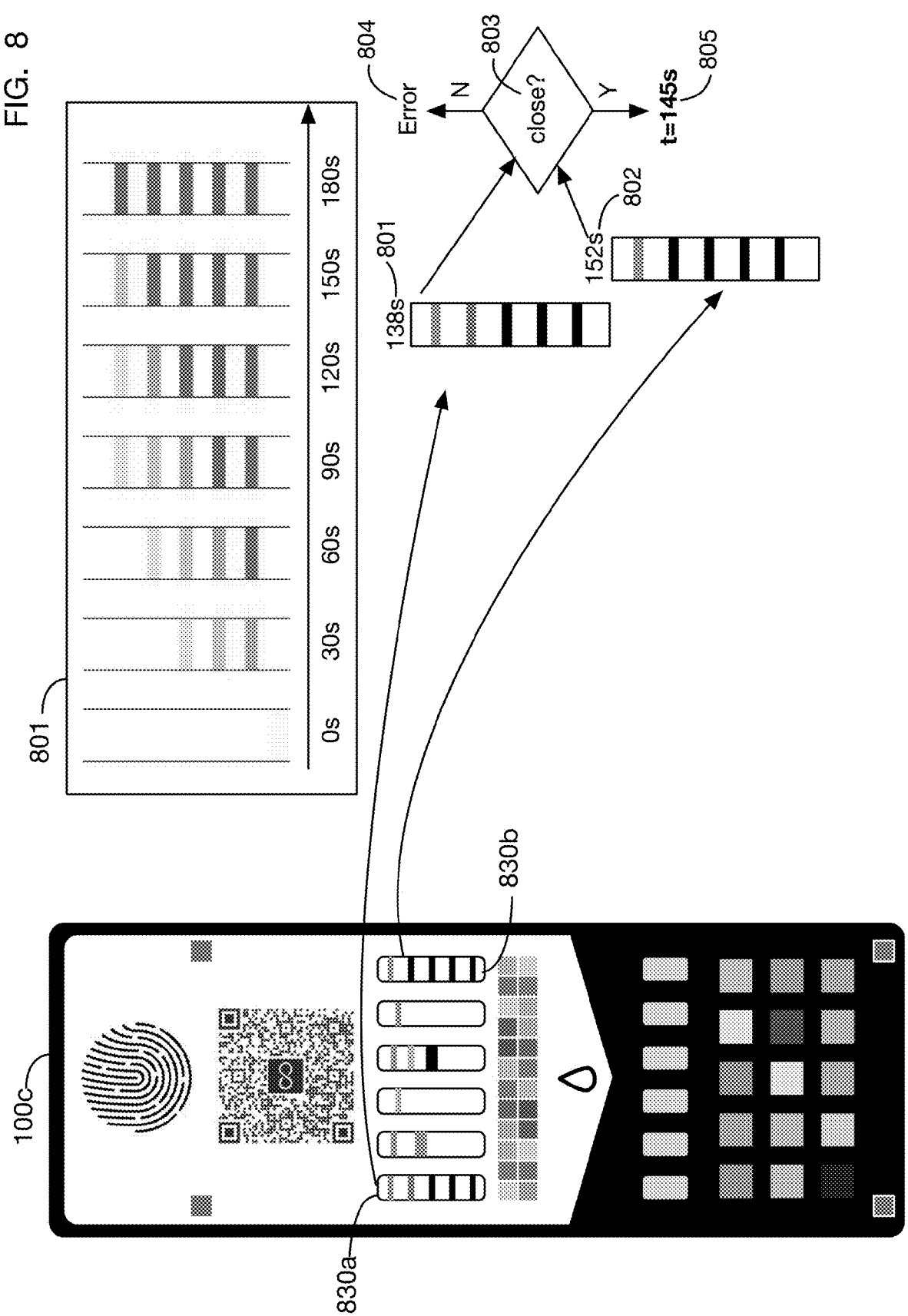

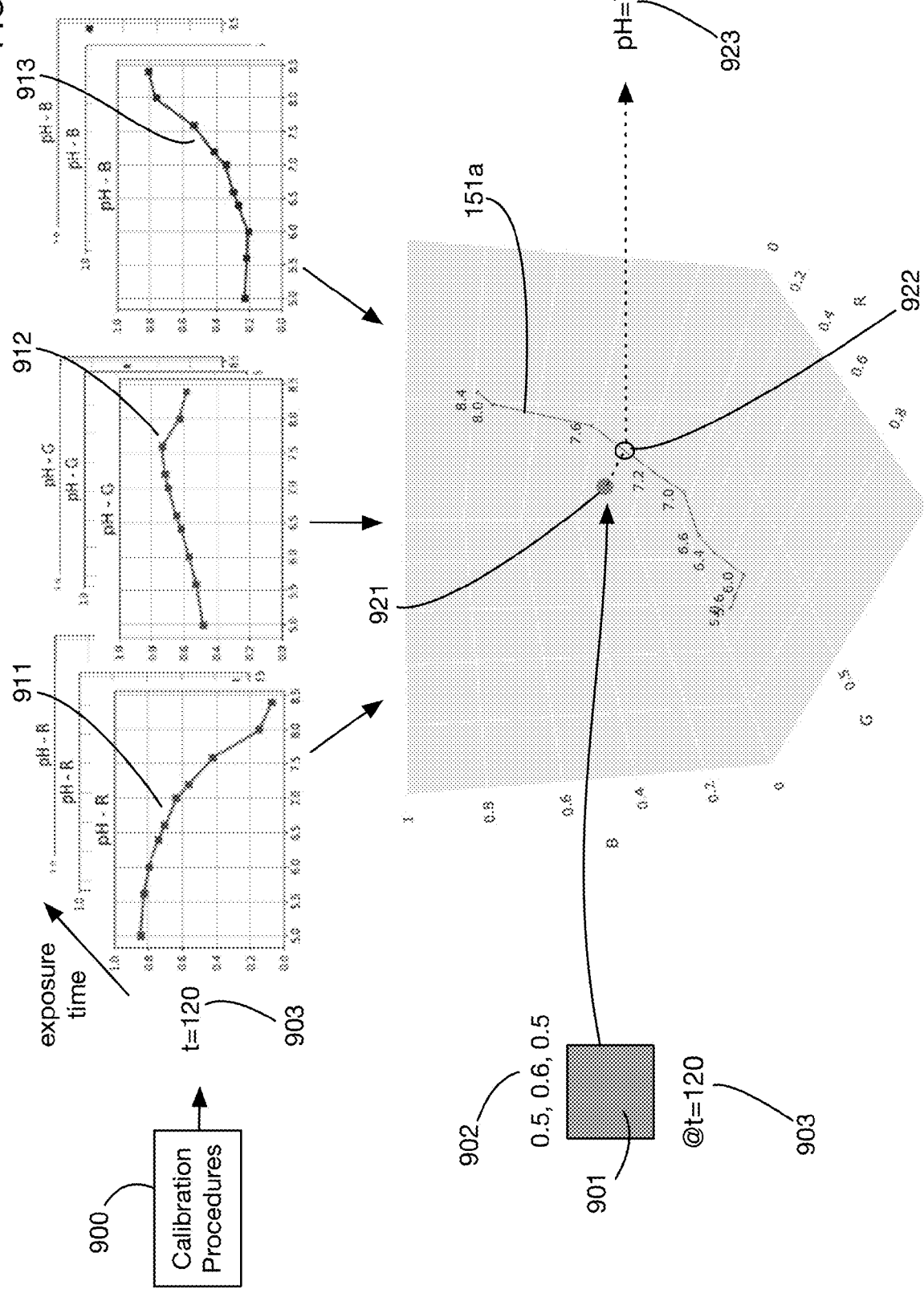

MULTI-FACTOR URINE TEST SYSTEM THAT ADJUSTS FOR LIGHTING AND TIMING

BACKGROUND OF THE INVENTION

Field of the Invention

One or more embodiments of the invention are related to the field of biochemical analysis of a body fluid, such as a urine or saliva sample. More particularly, but not by way of limitation, one or more embodiments of the invention enable a system that collects and analyzes a urine sample for multiple analytes, and that adjusts for variable lighting conditions and variable timing.

Description of the Related Art

Home urine testing systems such as dipsticks are available for certain tests, such as pregnancy tests. To be usable in a home environment by a consumer, a urine testing system must provide results that are easily interpreted by the user. This requirement has generally limited the types and complexity of urine tests that may be used in a home environment. For example, large panels of urine tests on a single test card cannot be easily interpreted by a user. In addition, certain types of tests indicate the presence or quantity of an analyte via subtle color or shade changes that a user may not be able to judge reliably.

To address these limitations, some systems have recently emerged that use smartphones to capture an image of a urine test card and to analyze the image to generate test results. A challenge with these systems is that the conditions under which the images are captured are not well controlled in a home environment, unlike in a laboratory. Key uncontrolled variables include lighting conditions and the time elapsed between exposing a test card to urine and capturing an image of the card. An illustrative system that uses a smartphone to analyze images of a urine test card is described in U.S. Pat. No 9,311,520, "Method and apparatus for performing and quantifying color changes induced by specific concentrations of biological analytes in an automatically calibrated environment." This patent describes a color correction process that attempts to adjust for variable lighting conditions; however, the method described in this patent assumes uniform lighting across the test card. In addition, this system does not address variation in the timing of image captures; instead it presumes that a user may be prompted to capture an image at an appropriate time. These limitations of this system and similar systems may reduce the accuracy of test results from urine tests in a home environment.

For at least the limitations described above there is a need for a multi-factor urine test system that adjusts for lighting and timing.

BRIEF SUMMARY OF THE INVENTION

One or more embodiments described in the specification are related to a multi-factor urine test system that adjusts for lighting and timing. One or more embodiments may for example enable home urine testing, and may compensate for variability in lighting conditions and time of exposure to urine that are more likely to occur in a home environment.

One or more embodiments of the invention include a test card and a test analyzer. The test card, which is exposed to a urine sample, may contain multiple test regions to test for multiple factors in the urine. Each test region may contain reagents that react with one or more substances in the urine sample, and that change appearance based on the presence or quantity of those substances. The test card may contain one or more time indicators that change appearance based on how long they are exposed to the urine sample. It may also contain multiple fiducial markers that may be used for lighting and color correction. Each fiducial marker may have a reference color that is measured in or defined with respect to a reference lighting condition.

The test analyzer may include a stored program or programs that execute on one or more processors. The user of a test card may capture an image of the card after exposing it to the urine sample, and after waiting for the reactions in the test regions to occur. This image may then be analyzed by the analysis program. The analysis program may extract from the image the appearance of the fiducial markers, the time indicator(s), and the test regions. It may generate a color adjustment that transforms the observed colors of the fiducial markers into their reference colors; this adjustment may therefore compensate for the variability of the lighting conditions under which the test card image is captured. The color adjustment may be applied to the appearance of the test regions, and potentially as well to the appearance of the time indicator(s). The analysis program may analyze the adjusted appearance of the time indicator(s) to determine how long the test card has been exposed to the urine sample.

Finally, the test program may calculate the presence or quantity of the substances of interest in each test region based on the adjusted appearance of the test region and on the calculated elapsed time of exposure to the urine sample.

In one or more embodiments, the color adjustment may be a function of the colors in the image of a region and of the position in the test card of the region. By including position as an input into the color adjustment function, the analysis system may be able to compensate for variability in lighting across the card.

One or more embodiments may use a linear color adjustment function, which may for example be a sum of a color factor, a position factor, and an offset. The color factor may be calculated as a product of a matrix and the color of a region in the image (as a 3 channel vector, for example). The position factor may be calculated as a product of a matrix and the position of the region in the image. The offset may be a vector added to the result for all regions.

In one or more embodiments, fiducial markers may include corner fiducials at the corners of a portion of the card containing the test regions. The reference colors of the corner fiducials may be identical. The fiducial markers may also contain multiple color fiducial markers. For example, in one or more embodiments there may be at least 3 color fiducial markers of different reference colors. One or more embodiments may have 9 or more color fiducial markers of different reference colors. One or more embodiments may have 12 or more color fiducial markers of different reference colors.

The linear color adjustment function may be calculated for example as a linear regression having inputs of the observed colors and positions of the corner fiducial and color fiducial markers, and having outputs of the reference colors of the fiducial markers.

In one or more embodiments the analysis system may analyze the image of the test card to identify certain lighting anomalies, which may for example make the image unusable; it may inform the user that the image is unusable, and may prompt for another image. For example, one or more embodiments may analyze the image for excessive glare. Glare may be detected for example if an area of the image has a color value that is very different from the color value of the area under the reference lighting condition. Glare may also or alternatively be detected if an area of the image has a color value that is very different from adjacent areas that should have similar values under the reference lighting condition.

Lighting anomalies may include shadows. One or more embodiments may analyze the image for shadows by comparing the color values of the corner fiducial markers; if these values are very different, the system may determine that part of the card is in shadow and generate a message that the image is unusable. For example, if the maximum value of the corner fiducials on a specific color channel (such as lightness) less the minimum value on that color channel exceeds a threshold, a shadow may be detected.

One or more embodiments of the test card may contain two time indicators. The elapsed time estimates from each of the time indicators may be compared; if they vary significantly then the system may determine that the test results are not valid. Elapsed time associated with a time indicator may be determined by comparing the adjusted appearance of the time indicator to a time indicator calibration sequence, which exposes a reference time indicator to urine for a sequence of known times and records the reference appearance at each time. Time indicators may be for example lateral flow assays with only non-human antibodies, so that human substances in the urine do not affect the appearance of the time indicators.

After adjusting test region appearances for lighting, and calculating exposure time, one or more embodiments may determine test results by comparing observed colors of test regions to a calibration curve for that type of test region. A calibration curve may be generated for example by exposing the reagents of a test region to different quantities of the substances being tested for, and observing the appearance of the test region under the reference lighting condition. Calibration curves may be calculated for different exposure times. The analysis system may obtain the calibration curve that corresponds to the elapsed time of exposure as measured for example by the time indicator(s). The test result indicating the presence or quantity of the substances may be determined based on the closest point on the calibration curve to the adjusted appearance of a test region.

In one or more embodiments the test card may contain an identifying code, such as for example a QR code. This code may indicate or be linked to information describing the test regions on the card. It may also indicate the manufacturing batch of the test card.

In one or more embodiments the test card may contain four or more lateral flow assays and fifteen or more colorimetric tests.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other aspects, features and advantages of the invention will be more apparent from the following more particular description thereof, presented in conjunction with the following drawings wherein:

FIG. 1A shows capture of an image of an illustrative urine test card under unknown lighting and timing conditions, and analysis of this image to determine test results.

FIG. 8 shows an illustrative method that may be used in one or more embodiments to calculate the elapsed time of exposure to a urine sample from the appearance of one or more time indicators on the test card.

FIG. 9 shows an illustrative calculation of a test result from color corrected images and from calibration curves.

DETAILED DESCRIPTION OF THE INVENTION

Figure 1B:
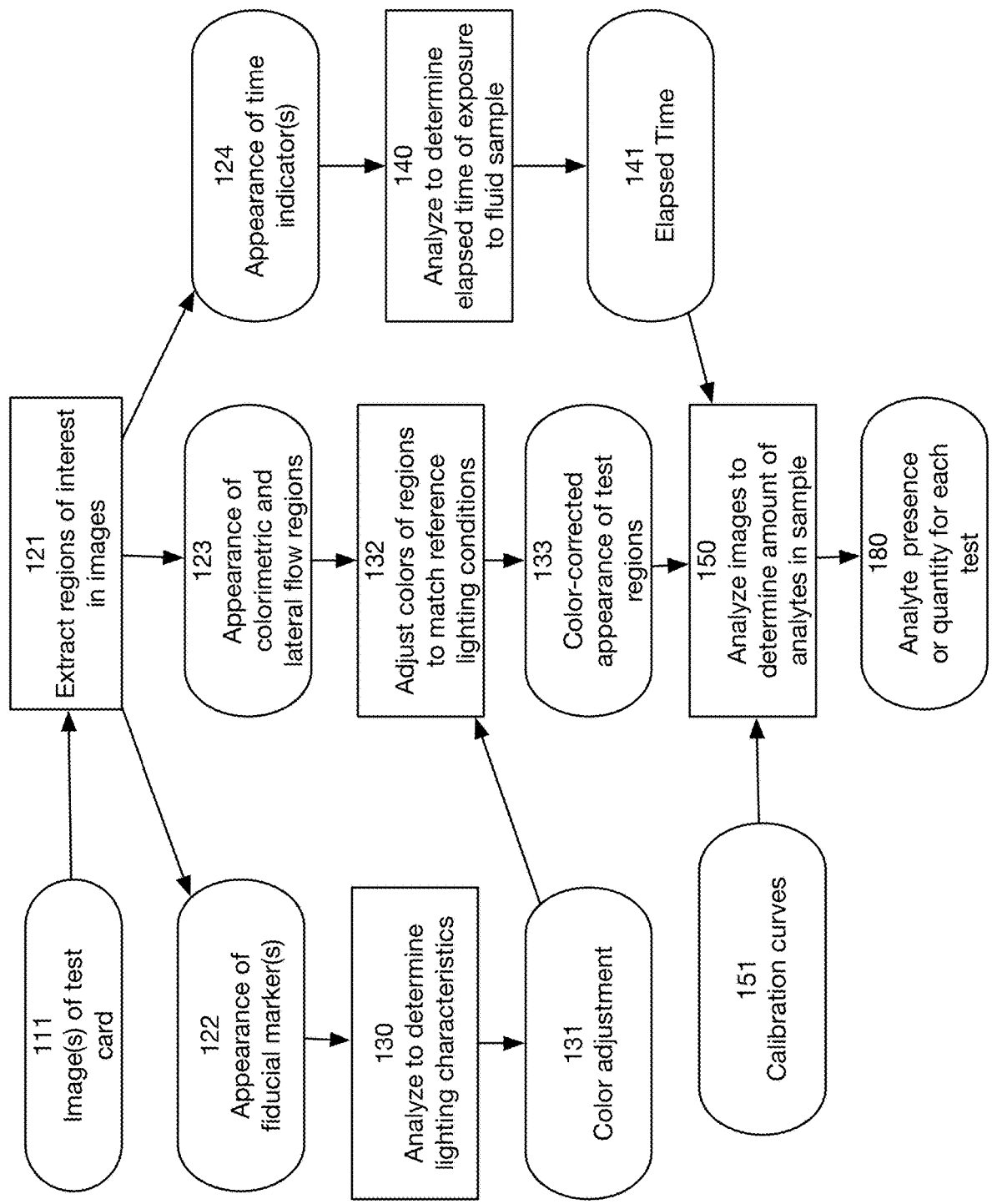
FIG. 1B shows a flowchart of processing steps performed by an illustrative embodiment of the invention to adjust for lighting and timing conditions.

A multi-factor urine test system that adjusts for lighting and timing will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

One or more embodiments of the invention may include a test card that contains one or more urine tests, and a test analyzer system that determines test results by analyzing an image of the test card after it has been exposed to a urine sample. FIG. 1A shows an illustrative test card 100 prior to exposure to a urine sample. The test card may contain various types of tests with reagents that react to specific analytes in a urine sample. The test regions on the test card may include for example colorimetric tests and lateral flow assays. The test card may also contain color fiducials for color correction, and one or more time indicators for timing correction, as described in detail below. FIG. 1A shows an illustrative use of the test card and test analyzer system. A user exposes test card 100 to a urine sample 101 (for example by dipping the end of the card into the sample, or by urinating directly on the card). The user then waits a period of time 102 for the reagents in each test region of the card to react with the urine sample, and then captures an image (or images) 111 of the test card 100a (after exposure). This image may be captured for example using a smartphone 110 or similar device. Device 110 may be for example, without limitation, a smart phone, a smart watch, a tablet, a laptop computer, a notebook computer, a desktop computer, smart glasses, a virtual reality headset, a specialized chemistry reader, or any combination of these devices. In one or more embodiments a user may capture an image 111 using any camera or cameras, and then upload this image to another system or systems for analysis.

Because the test card 100 may be used in a home environment, instead of a laboratory, the lighting conditions 103 under which image 111 is captured may be variable and uncontrolled. This variability presents a specific challenge for the analysis of the test image; solutions to this challenge are described below. Another challenge is that the amount of time 102 that elapses between exposure of test card 100 to urine sample 101 and the capture of image 111 may be variable and uncontrolled. Even if the system prompts the user to capture an image after a specific amount of time, there is variation on when the user starts the timer for this prompt and how long the card was exposed to urine before beginning this process. User reaction times and other delays may affect the amount of time 102. Solutions to the challenge of timing variability are also described below.

Image 111 is then analyzed by a test analyzer that includes an analysis program 115, which determines the results of the tests integrated into test card 100. These results 180 may be displayed for example on device 110 or on any other device. The analysis program may be stored on and may execute on the image capture device 110 (such as a smartphone), or on any other processor or combination of processors. For example, some or all of the analysis may be performed by programs executing on servers that receive the image 111 or data from the image via an internet connection to device 110. In one or more embodiments some of the image analysis may be performed locally on device 110, and some may be performed remotely (for example on cloud-connected servers). In one or more embodiments all of the image analysis may be performed locally on device 110. In one or more embodiments all of the image analysis may be performed remotely (for example on cloud-connected servers).

FIG. 1B shows illustrative processing steps that may be performed in one or more embodiments of analysis program 115. As described above, these steps may be performed by a stored program or programs executing on any processor or combination of processors. One or more images 111 of the test card may be input into step 121, which extracts regions of interest from the image(s). Extraction 121 may include geometric transformations on the image to correct for angular distortion (for example if the user holds the card at an angle relative to the camera) or for camera distortions. Outputs of extraction step 121 may include for example appearance of fiducial markers 122, appearance of test regions on the test card 123 (such as lateral flow assay regions and colorimetric test regions), and appearance of time indicator(s) 124. Other regions of interest that may be extracted may include regions containing identifying information on the card such as a bar code or QR code.

Appearance of fiducial markers 122 may then be analyzed in step 130 to determine the lighting conditions under which the image 111 was captured. This analysis results in a color adjustment function or procedure 131, which may for example transform observed colors in regions of the test card to colors that would be observed under reference lighting conditions. This transformation may be performed in step 132, which adjusts the appearance 123 of the test regions of the card, resulting in color-corrected appearances 133 of these test regions.

Appearance of time indicator(s) 124 may be analyzed in step 140 to determine the elapsed time 141 between exposure of the test card to the urine sample and the capture of the test image(s) 111.

The color-corrected appearances 133 and the elapsed time 141 may then be used in step 150 to determine the presence or amounts of analytes in the urine sample. This step 150 may use calibration curves 151 that relate the analyte amounts to the expected appearance of each region as a function of elapsed time. The output of step 150 is the test results 180 with the presence or quantity of each analyte.

Figure 2:
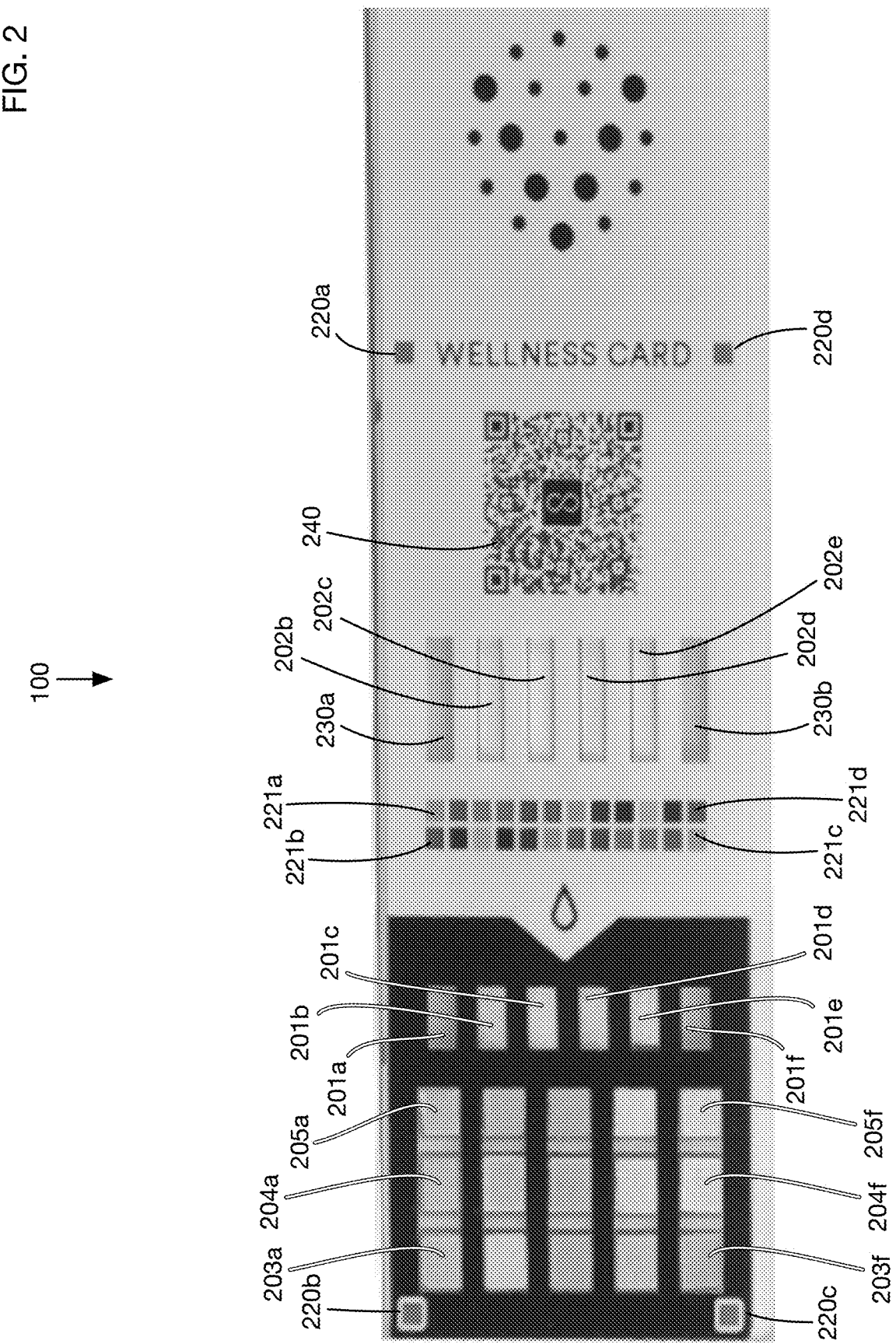
FIG. 2 shows an illustrative urine test card that integrates lateral flow tests, colorimetric tests, color fiducials for color correction, and timing strips for timing correction.

FIG. 2 shows an image of an illustrative test card 100 that may be used in one or more embodiments of the invention. This illustrative card has 4 lateral flow assay test regions 202b, 202c, 202d, and 202e, and it has 15 colorimetric test regions such as regions 203a, 204a, and 205a shown at the top and regions 203f, 204f, and 205f shown at the bottom. One or more embodiments may have any type of test regions, including but not limited to lateral flow and colorimetric tests. Each test region may contain reagents or combinations of reagents that react with specific elements that may be present in a urine sample to generate a visible change in the appearance of the test region.

Test regions may be exposed directly to a urine sample, or they may receive the urine sample for example from another pad or chamber to which urine is added. For example, urine may be wicked along a pad from one point in the test card to another. In the illustrative embodiment 100 shown in FIG. 2, the colorimetric test regions (203a through 205f) are exposed directly to the urine sample. The lateral flow assay regions 202b through 202e receive urine from corresponding pads 201b, 201c, 201d, and 201e. These pads have a small portion that is exposed through the cover of the test card, and the remainder of the pads form a wicking channel that carries urine to the corresponding lateral flow assays. One or more embodiments may route urine fluid on the test card using any desired method, such as wicking pads, capillaries, or microfluidic channels of any type.

Illustrative test card 100 contains several fiducial markers that may be used to adjust the appearance of card images for varying lighting conditions. The fiducial markers may also be used in one or more embodiments to correct the geometry of captured images since the markers may be in known positions and orientations on the card. Card 100 has four corner fiducial markers 220a, 220b, 220c, and 220d. The test regions are contained in the area bounded by these corner fiducial markers. A benefit of placing fiducial markers at the boundary of the test regions is that variation in lighting conditions across the card may be more easily detected. In this embodiment, the corner fiducial markers 220a through 220d are all of the same color, which is a neutral gray. In one or more embodiments the corner fiducial markers may be of any color or colors, and of any size and shape.

Test card 100 also contains two rows of color fiducial markers such as 221a and 221b at the top of the image in FIG. 2, and 221c and 221d at the bottom of the image in FIG. 2. In this illustrative embodiment there are 24 color fiducial markers. These are of various colors, with some repetition of colors in the embodiment shown in FIG. 2. In one or more embodiments, color fiducial markers may be located anywhere on test card 100; they may be of any colors, sizes, and shapes. One or more embodiments may have any number of color fiducial markers and any number of distinct colors for these markers. For example, in one or more embodiments there may be 3 or more color fiducial markers with 3 or more distinct colors. In one or more embodiments there may be 9 or more color fiducial markers with 9 or more distinct colors.

In one or more embodiments there may be 12 or more color fiducial markers with 12 or more distinct colors.

Test card 100 has two time indicators 230a and 230b. In this embodiment, these time indicators are specialized lateral flow assays that change appearance as a function of the time of exposure to a urine sample, regardless of the contents of the sample. These time indicators 230a and 230b receive urine from pads 201a and 201f, respectively. A potential benefit of having two (or more) time indicators is that the redundancy may be used to validate the exposure time estimates. For example, if the two time indicators 230a and 230b indicate substantially different exposure times, the results from the test card may be questionable. Placing the two time indicators on opposite edges of the card also helps assure that urine exposure and flow is similar throughout the card.

Test card 100 also has a QR code 240 which may uniquely identify the card or the type of card. This code may contain or may be linked for example to information on the tests on the card, to the manufacturing date and batch, or to any other information used for analysis or quality assurance.

Figure 3B:
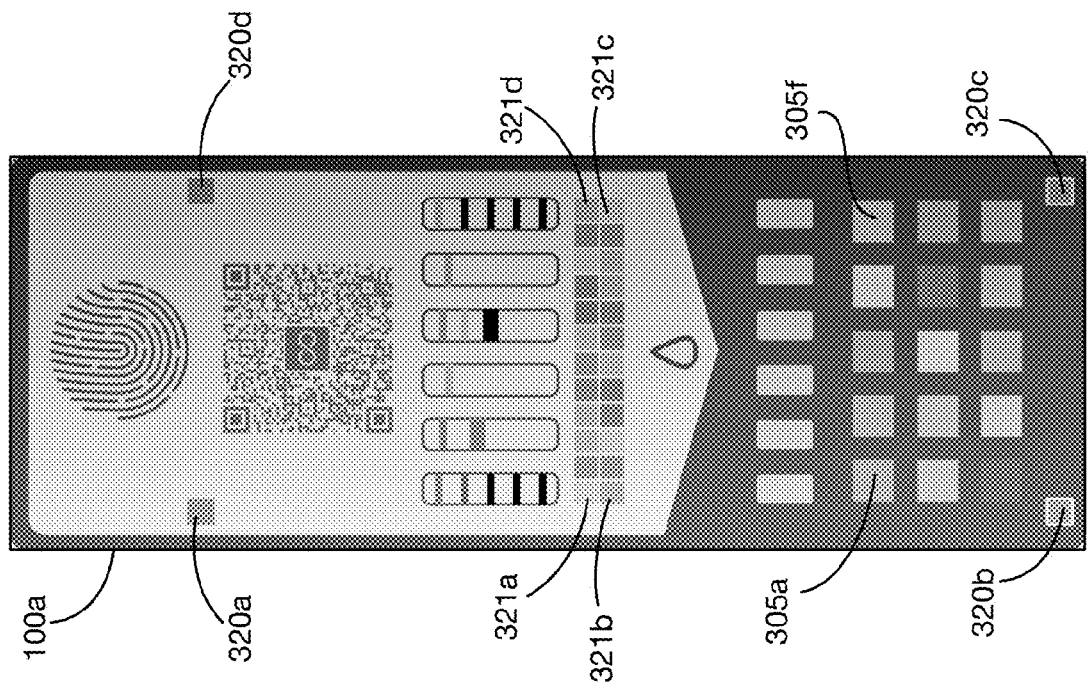
FIG. 3B shows the test card of FIG. 3A after exposure to urine, imaged under lighting conditions that differ from the reference conditions.
Figure 3A:
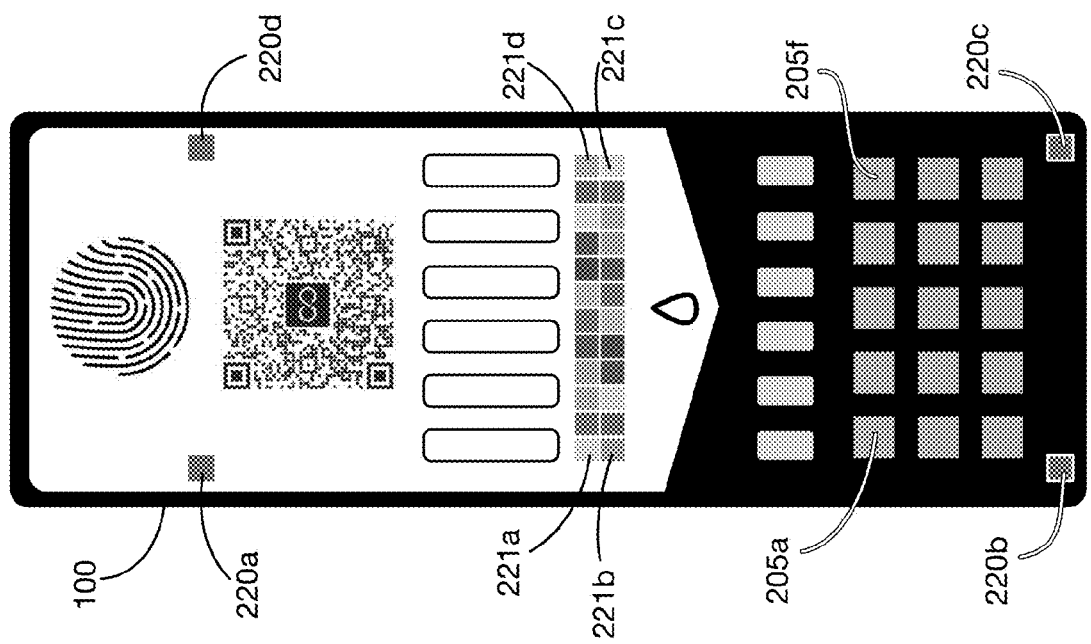
FIG. 3A shows a diagram of the test card of FIG. 2 under reference lighting conditions, prior to exposure to urine.

Turning now to lighting adjustment methods, FIGS. 3A through 5B show an illustrative adjustment method that may be used in one or more embodiments. FIG. 3A shows test card 100 prior to exposure to a urine sample. The image of the test card in FIG. 3A is shown under a standard reference lighting condition. The fiducial markers on the test card may be constructed to have known colors under this reference condition. (These reference colors may be determined in a color calibration step, for example, by measuring the colors of each fiducial marker under the reference conditions.) In one or more embodiments, manufacturing methods for the test cards may be controlled to ensure that colors of each color fiducial do not deviate beyond a threshold from the reference color standard for each fiducial. These manufacturing methods may include for example using specific inks and printing processes for color uniformity, and performing quality control on the test cards to measure the color deviations.

Illustrative reference colors for the fiducial markers are as follows, expressed as triplets of (red, green, blue) intensity in the range 0 to 255. These colors are exemplary; one or more embodiments may use fiducials of any reference colors. Corner fiducial markers each have reference colors (120, 120, 120). The two rows of color fiducial markers have the following reference colors:

| Top Row | | | | | | | | | | | |
|---|---|---|---|---|---|---|---|---|---|---|---|
| R: | 210 | 80 | 80 | 160 | 160 | 240 | 240 | 80 | 80 | 160 | 120 | 175 |
| G: | 210 | 160 | 240 | 160 | 80 | 80 | 160 | 80 | 80 | 240 | 120 | 175 |
| B: | 210 | 80 | 80 | 240 | 80 | 80 | 160 | 160 | 240 | 160 | 120 | 175 |
| Bottom Row | | | | | | | | | | | |
| R: | 175 | 120 | 160 | 80 | 80 | 240 | 240 | 160 | 160 | 80 | 80 | 210 |
| G: | 175 | 120 | 240 | 80 | 80 | 160 | 80 | 80 | 160 | 240 | 160 | 210 |
| B: | 157 | 120 | 160 | 240 | 160 | 160 | 80 | 80 | 240 | 80 | 80 | 210 |

In this illustrative embodiment, the colors of the bottom row of color fiducial markers are the same as those of the top row, but in the opposite order. Thus there are 12 distinct colors for the 24 color fiducial markers, with 2 fiducial markers for each of these 12 colors. Repeating colors at offset locations may assist in developing a color correction function that incorporates location on the card, as described below.

One or more embodiments may use fewer color fiducial markers than the 24 color fiducial markers shown in FIG. 3A. For example, one or more embodiments may use 3 color fiducial markers of different colors, such as for example markers of pure red (RGB of (255, 0, 0)), pure green (RGB of (0, 255, 0)), and pure blue (RGB of (0, 0, 255)). One or more embodiments may use 9 color fiducial markers of different colors, such as for example 3 markers with 3 different shades of red (such as RGB values of (160, 80, 80), (240, 80, 80), and (240, 160, 160)), 3 markers with 3 different shades of green (such as RGB values of (80, 160, 80), (80, 240, 80), and (160, 240, 160)), and 3 markers with 3 different shades of blue (such as RGB values of (80, 80, 160), (80, 80, 240), and (160, 160, 240)). These configurations and numbers of color fiducial markers are illustrative. Any number of color fiducial markers with any set of colors, including possible repeats of certain colors, may be used in one or more embodiments of the invention.

FIG. 3B shows an illustrative image 100a of card 100 after exposure to urine (for a period of time), captured under lighting conditions that deviate significantly from the reference lighting conditions illustrated in FIG. 3A. Lighting in image 100a is also not uniform across the test card. Regions of the image 100a that correspond to fiducials on test card 100 are as follows: 320a through 320d are images of corner fiducial markers 220a through 220d, respectively; and 321a through 321d are images of illustrative color fiducial markers 221 through 221d, respectively. (For ease of illustration only 4 of the 24 color fiducial markers are labeled.) Colorimetric test regions 205a and 205f have corresponding images 305a and 305f in image 100a. (For ease of illustration only 2 of the 15 colorimetric test regions are labeled.)

Figure 4:
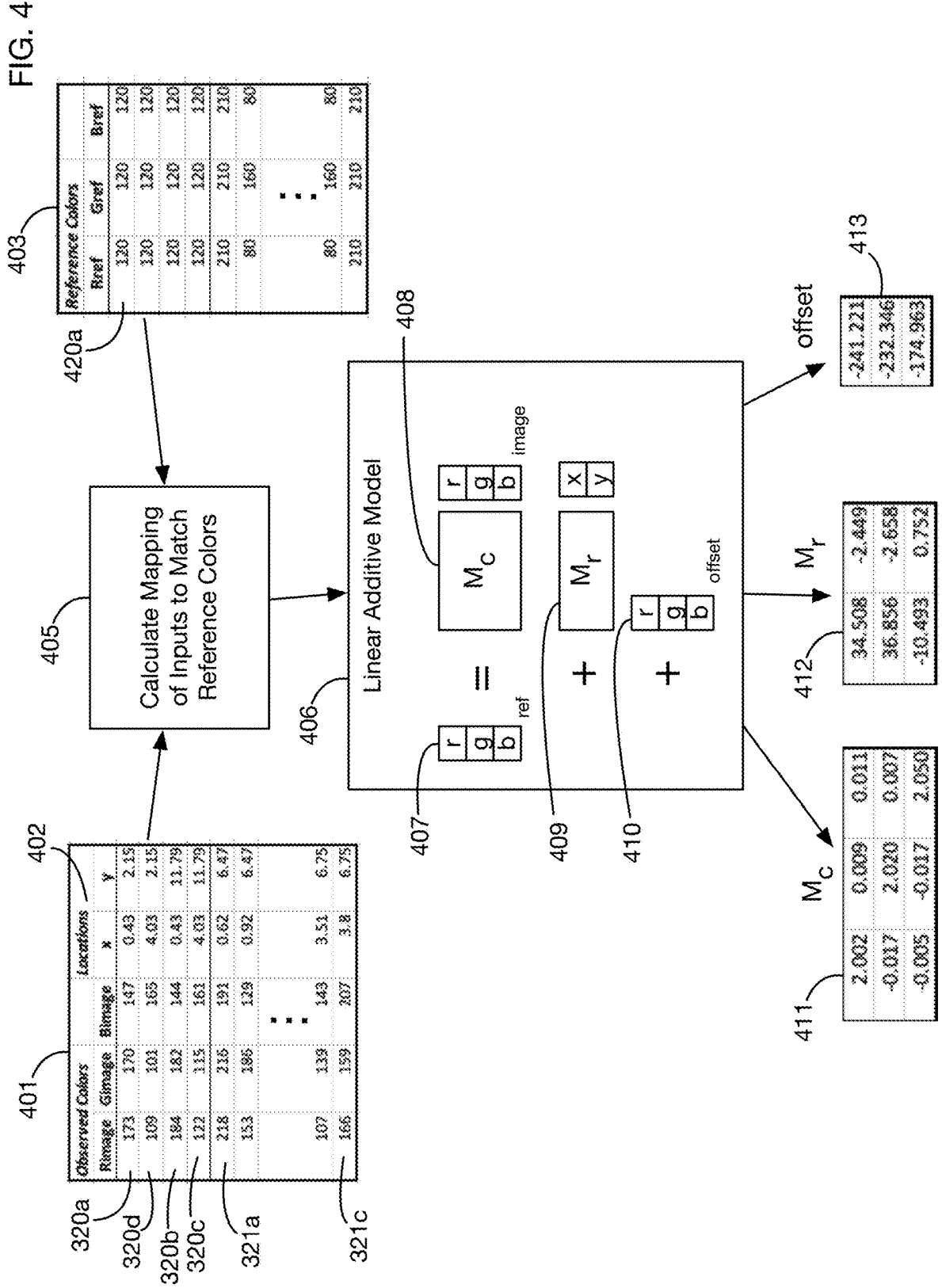
FIG. 4 shows an illustrative model for color correction that may be used in one or more embodiments.
Figure 5:
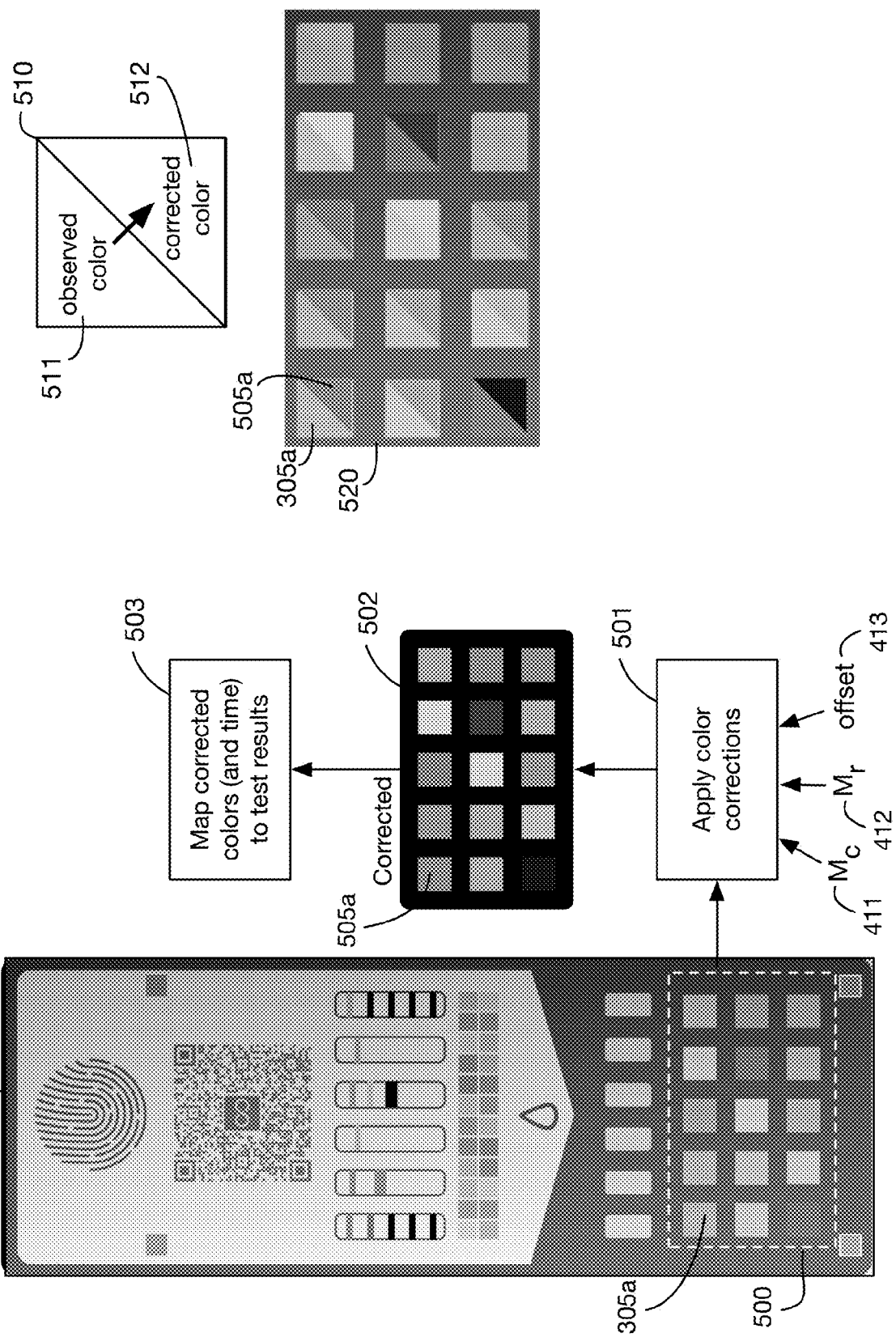
FIG. 5A shows application of the correction model of FIG. 4 to the image of FIG. 3B.
FIG. 5B compares color corrected and uncorrected images of the colorimetric tests of the test card.

FIG. 4 shows an illustrative method that may be used to derive color corrections to image 100a. The intent of the color correction process is to transform the appearance of the regions of interest in image 100a into their projected appearance under reference lighting conditions. One or more embodiments may use any desired method to determine an appropriate transformation. For example, any type of function approximation or estimation method may be used to generate a function that maps appearances into color-corrected appearances. FIG. 4 illustrates an embodiment that estimates a linear function that maps observed colors into corrected colors. This function also takes into account the position of each region of interest on the test card. A benefit of using the position as an input to the color correction function is that the correction may then compensate for non-uniform lighting conditions across the card. The use of a linear function is illustrative; one or more embodiments may use any type of linear or nonlinear function to perform color corrections.

Calculation 405 to determine the correction function receives as inputs a table 401 of the observed colors and known locations of each fiducial marker in the card, and the corresponding reference colors 403 for each fiducial marker. The locations 402 of each fiducial marker may for example be the offsets of the center of each marker from a fixed reference point on the card. Location coordinates may be measured in any units, such as for example, without limitation, pixels, millimeters, centimeters, meters, or inches. For locations that are measured in pixels, the (x,y) location values 402 may be for example integer values in one or more embodiments; for other units the location values 402 may be for example decimal values of any desired precision. Illustrative observed RGB values and locations are shown in table 401 for the corner fiducial images 320a through 320b, and for illustrative color fiducial images 321a and 321c.

(The complete table may contain entries for each corner fiducial and each color fiducial, and possibly for other points on the card with known reference colors.) Table 403 contains reference colors such as those presented above. This example uses a linear additive model 406 for the mapping function from inputs 401 to outputs 403. This linear model has a parameter matrix 408 that transforms the RGB vector of observed colors into reference colors, a parameter matrix 409 that maps location vectors (x,y) into color variations, and an overall offset RGB vector 410. The location effect matrix 409 may vary based on the units in which locations vectors (x,y) are measured; for example, if the units of the location vectors are changed from pixels to millimeters, the matrix 409 may change by a scaling factor. The model 406 is additive in that the effects of the matrix multiplication 408, the matrix multiplication 409, and the offset 410 are added to obtain the final corrected color 407. Techniques such as linear regression may be used to estimate the matrices 408 and 409 and the offset 410. For the data 401 and 403, the resulting parameters for the best fit linear additive model are 411, 412, and 413.

One or more embodiments of the invention may use other functional models besides or in addition to the linear additive model 406 of FIG. 4. For example, in one or more embodiments the effect of position on color may be multiplicative instead of additive. One or more embodiments may separate the test card into zones and fit color correction functions separately for each zone. One may use machine learning techniques to obtain a mapping based for instance on a neural network or other function approximation system. One or more embodiments may use any color space in addition to or instead of RGB, such as for example HSV, HSL, or CIELAB. One or more embodiments may use other information to derive a color correction function, such as ambient light conditions sensed by a user's phone or by another image capture device. Any method that derives a mapping from observed colors to reference colors, which may optionally use other inputs such as location or ambient light sensor data, is within the spirit of the invention.

FIGS. 5A and 5B show application of the model derived in FIG. 4 to correct the colors of the image 100*a* of test card 100. The observed colors of regions of interest from image 100*a* are input into color correction process 501 along with the parameters 411, 412, and 413 derived from the appearance of the fiducial markers. For example, the 15 colorimetric test regions 500 are corrected by mapping 501 to corrected colors 502; illustrative image 305*a* of the upper left colorimetric test is corrected to image 505*a*. The corrected colors 502 are then input into process 503 that calculates test results based on the corrected colors (and on the calculated elapsed time), as described below. FIG. 5B shows the uncorrected and corrected colors of the colorimetric tests side-by-side for comparison, with legend 510 showing that the observed color 511 is shown in the upper left of the square and the corrected color 512 is shown in the lower right of the square. Table 520 shows this comparison for each of the colorimetric test regions.

Figure 6:
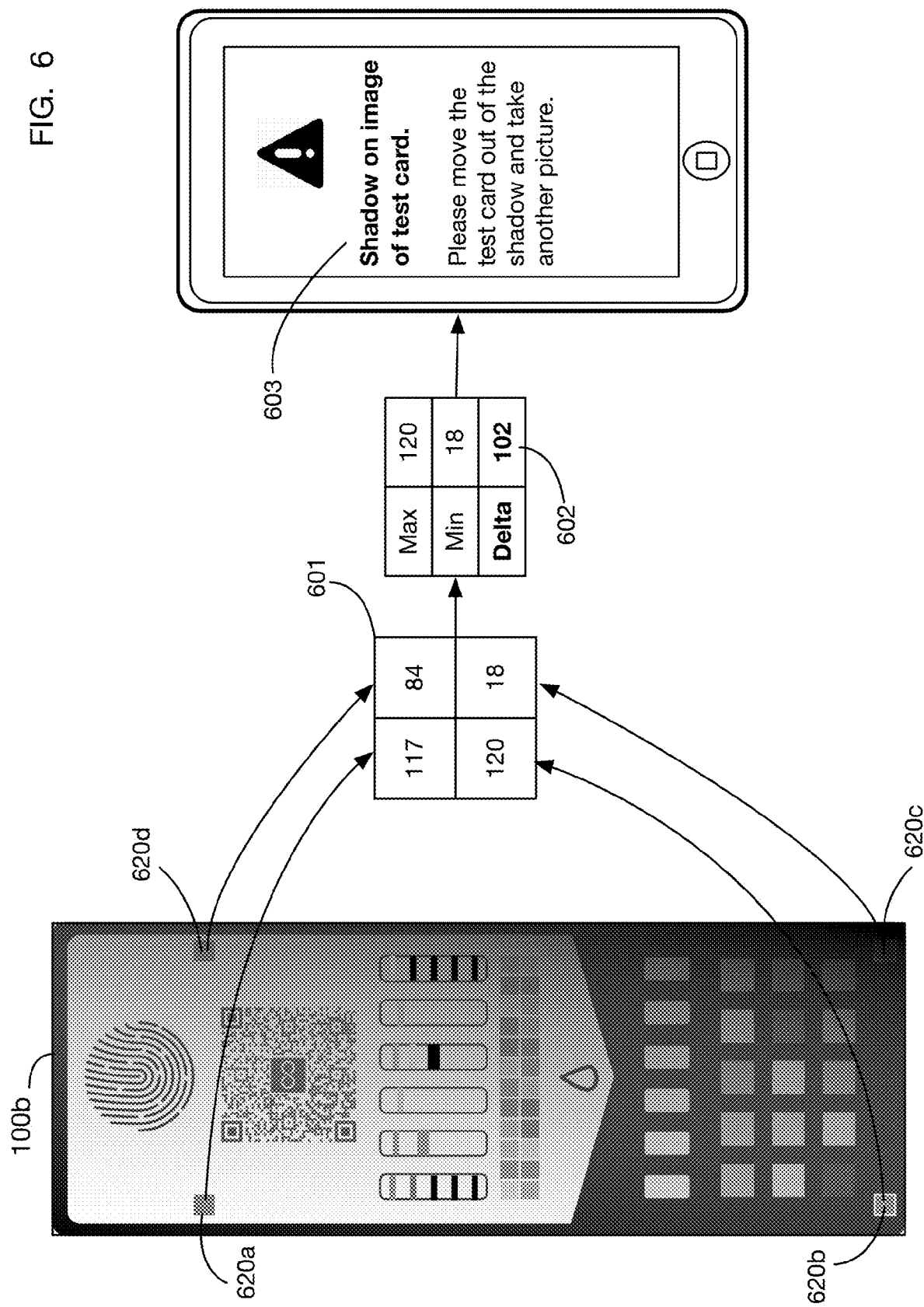
FIG. 6 shows an illustrative method that may be used in one or more embodiments to detect shadows on the test card and to inform the user that another image is needed.

In addition to color correction, one or more embodiments may analyze lighting conditions and patterns on the test card to determine whether light is sufficiently uniform or otherwise of sufficient quality for valid test results to be calculated. If issues are discovered with the lighting conditions, and these issues cannot be corrected during analysis, the system may generate an indication for the user that the captured image may not be usable. The system may prompt the user to capture another image (or to repeat the test altogether with another test card). FIG. 6 shows an illustrative example that detects a shadow on test card image 100*b*. One method that may be used to detect shadows is to compare the observed colors of the four corner fiducial markers; a large variance across the four fiducials may indicate a shadow. In the embodiment shown in FIG. 6, a single color value is calculated and compared for each of the four corner fiducial markers. This method is illustrative; one or more embodiments may use any combination of color channels or any single color channel (in any color space) to detect lighting anomalies. In this example, the single color value is a grayscale value. This grayscale value may be calculated using any desired transformation of RGB to grayscale; for example it may be a simple average of the R, G, and B color channels or a more complex weighted average. One or more embodiments may use any other color channel or combination thereof, such as for example lightness in an HSL color space. Grayscale values for corner fiducial images 620*a* through 620*d* are shown in table 601. A simple measure of variance for the four grayscale values may be for example the difference 602 between the maximum and minimum value. If this difference exceeds a threshold value, the system may determine that one part of the test card is heavily shadowed compared to another, and a message 603 may be displayed to the user asking the user to capture another image. In this situation, the time indicator (s) on the test card may be extremely important since the user may be capturing another image after additional elapsed time of exposure to the urine sample. Without a time indicator, capturing and using another image if the first image is unusable may not be feasible, and the entire test card may be wasted.

Figure 7:
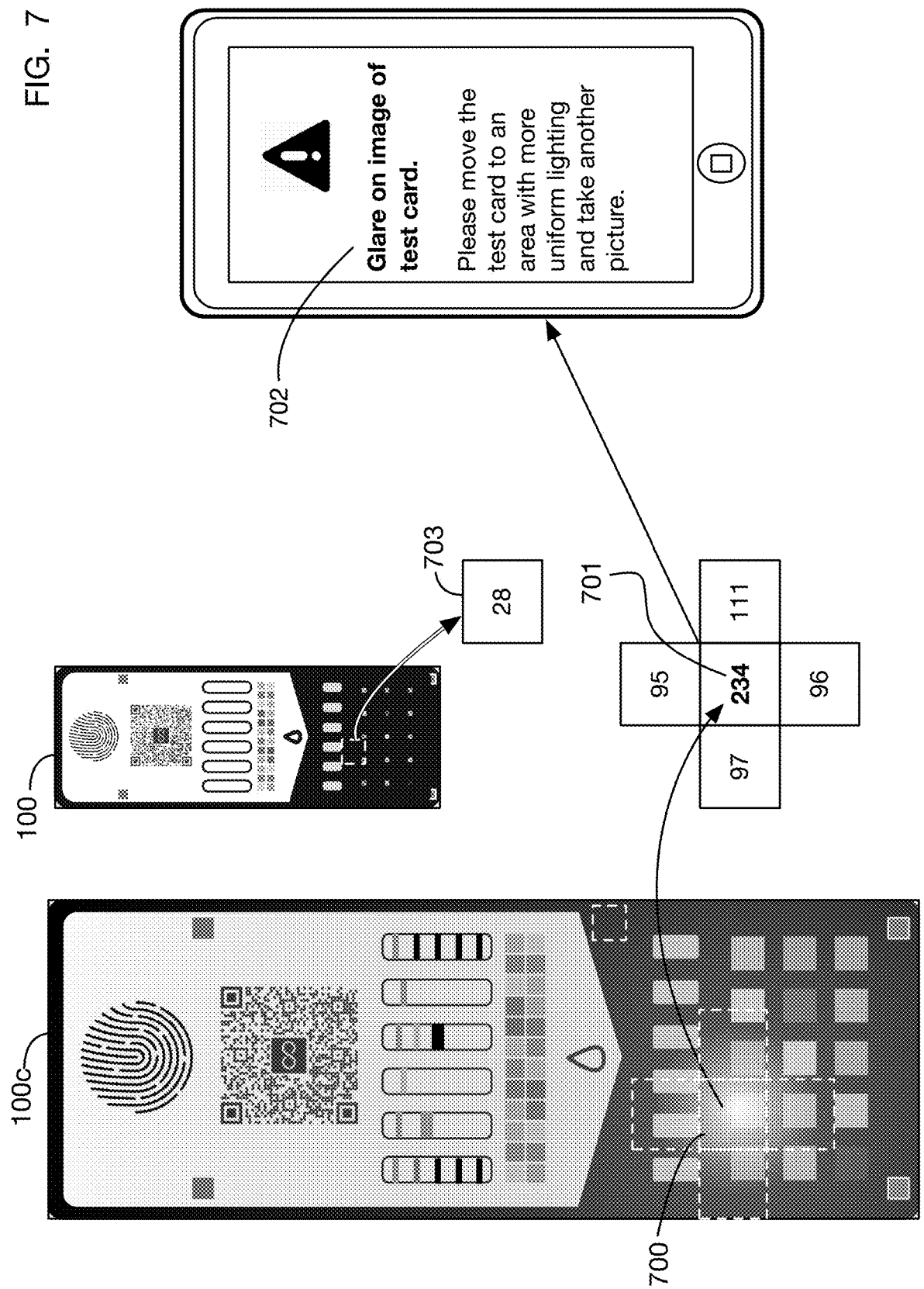
FIG. 7 shows an illustrative method that may be used in one or more embodiments to detect glare on the test card and to inform the user that another image is needed.

FIG. 7 shows an illustrative embodiment of a method to detect another lighting anomaly in a test card image. This example shows glare detection. Glare may be defined for example as a region of a test card image 100*c* that is much brighter or lighter than nearby regions that have similar colors or brightness under reference lighting conditions. As with shadow detection, one or more embodiments may use any color channel or combination of color channels to detect glare. The example shown in FIG. 7 uses grayscale values. For example, region 700 of test card image 100*c* has grayscale value 701 which is substantially greater (brighter) than the grayscale value of the surrounding regions (for example the regions above, below, left, and right). If this difference between the grayscale value of a region and that of surrounding regions exceeds a threshold value, a message 702 may be transmitted to the user indicating that glare is detected and that the user should capture another image since the existing image is not usable. In one or more embodiments, glare may be defined instead as an excessive difference between the observed value 701 of a region and the expected value 703 of that region under reference lighting conditions.

FIG. 8 illustrates how the time indicator or indicators of a test card may be used in one or more embodiments to calculate the elapsed time of exposure to a urine sample. In this illustrative embodiment, the test card has two time indicators; in image 100*c* of the test card (after exposure) these two time indicators have appearances 830*a* and 830*b*. In one or more embodiments these time indicator appearances may be color corrected as described above for colorimetric test regions; color correction is not shown in FIG. 8 for ease of illustration. In this embodiment, time indicators are lateral flow assays with multiple target lines that become visible as the urine sample flows along the assay membrane. The number of visible lines and the intensity of the lines varies with the time of exposure. The time indicator may for example use antibodies that are non-human (such as donkey-anti-goat and goat-anti-mouse), and may use no human antibodies, which means they should not be sensitive to human variables; thus the intensity of the target lines in the time indicator will be affected only by exposure time and not by the presence or absence of specific analytes in the urine sample. (These antibodies may also be used for control lines in other lateral flow assays on the test card.)

The time indicators may be configured to minimize the effect of environment factors such as temperature and humidity on the visibility and intensity of test lines, so that the timing factor can be isolated and measured. Within the expected range of ambient temperatures during use, temperature should not have a significant impact on the time indicator results. In case of extreme high or low temperatures, the timer will be affected the same as the lateral flow strips thereby doubling as a control for ambient temperature. If the user's phone can sense ambient temperature, that information can also be used in one or more embodiments to adjust results for extreme temperatures or other environmental factors.

The relationship between visibility and intensity of test lines and exposure time may be determined for example using calibration experiments. Table 801 shows an illustrative calibration run showing the appearance of test lines of a reference time indicator at different elapsed times to a reference urine sample. Using this calibration data 801, one or more embodiments may obtain an elapsed time estimate by finding a closest match between the observed intensity of test lines and a point on the calibration curve 801. Interpolation may be performed between points on the curve 801 if the observed test line intensities lie between two values. For example, test indicator 830a may correspond to an interpolated elapsed time 801, and test indicator 830b may correspond to an interpolated elapsed time 802. In one or more embodiments, elapsed times from multiple time indicators may be compared in test 803, and if they are too far apart it may indicate an error 804 (for example because the urine sample was not distributed uniformly across the test card). If values are reasonably close, a combined estimate 805 may be generated, for example as an average of the elapsed time estimates from the different time indicators.

FIG. 9 shows an embodiment of a calculation of a test result from color-corrected appearance and from the time estimate obtained from time indicators. For illustration this calculation is shown for a colorimetric test; a similar procedure may be used for a lateral flow assay or other test region. The color-corrected appearance 901 of a colorimetric test region may be expressed as a triplet of RGB values 902 (shown here in the range of [0,1] for each color channel). An elapsed time estimate 903 is available from analysis of the time indicator or indicators on the test card. The color 902 and time 903 are compared to a sequence of calibration curves that are generated for example using calibration procedures 900. These calibration procedures 900 may for example measure the color of a colorimetric test region with different quantities of the test analyte in the sample, and at different exposure elapsed times. For example, the illustrative calibration curves 911, 912, and 913 show the R, G, and B colors, respectively, as a function of sample pH, after an exposure elapsed time of 903. Similar curves are obtained for other exposure times. For a specific elapsed time 903, the three curves 911, 912, and 913 may be combined into a 3D curve 151a in RGB space; each point on this curve corresponds to a pH value. The observed color 902 maps to a point 921 in this 3D RGB space. One or more embodiments may for example locate the point on curve 151a that is closest to the observed color point 921, and use that point as the test result. If this point lies between calibration points, a result value 923 may for example be calculated by interpolating between points on the curve corresponding to known pH values. One or more embodiments may use any method to interpolate between calibration points, including but not limited to linear interpolation.

While the invention herein disclosed has been described by means of specific embodiments and applications thereof, numerous modifications and variations could be made thereto by those skilled in the art without departing from the scope of the invention set forth in the claims.

What is claimed is:

1. A multi-factor urine test system that adjusts for lighting and timing, comprising:
   a test card comprising
      a plurality of test regions,
         wherein said plurality of test regions comprise lateral flow assay regions and colorimetric test regions;
         wherein said lateral flow assay regions are located on a separate portion of said test card than said colorimetric test regions, such that said lateral flow assay regions differ than said colorimetric test regions;
         wherein each test region comprises one or more reagents configured to
            react with one or more substances that may be present in a urine sample to which each test region is exposed; and
            change appearance based on a presence of or a quantity of the one or more substances in the urine sample;
      at least one time indicator configured to change appearance based on a duration of time that the at least one time indicator is exposed to the urine sample;
      a plurality of fiducial markers, each fiducial marker of the plurality of fiducial markers comprising a reference color that is measured under a reference lighting condition, and wherein the plurality of fiducial markers comprises
         corner fiducial markers, wherein each corner fiducial marker of said corner fiducial markers is located at a corner of a region of the test card that contains the plurality of test regions, such that the corner fiducial markers are located at a boundary of the plurality of test regions and such that the plurality of test regions are contained in an area bounded by said corner fiducial markers;
   a test analyzer comprising a stored program configured to execute on one or more processors,
      wherein the stored program is configured to
         receive an image of the test card captured after the test card is exposed to the urine sample;
         analyze the image of the test card to extract
            an appearance of each fiducial marker of said plurality of fiducial markers in the image;
            an appearance of each test region in the image; and
            an appearance of the at least one time indicator in the image;
         analyze the appearance of each fiducial marker of said plurality of fiducial markers in the image to generate a color adjustment that transforms colors in the image to adjusted colors under the reference lighting condition;

apply the color adjustment to the appearance of each test region in the image to generate an adjusted appearance of each test region;

analyze the appearance of the at least one time indicator to determine an elapsed time between exposure of the test card to the urine sample and capture of the image;

for each test region, calculate the presence of or the quantity of the one or more substances in the urine sample based on
the adjusted appearance of each test region; and, the elapsed time between exposure of the test card to the urine sample and capture of the image.

2. The system of claim 1, wherein
the color adjustment comprises a function of the colors in the image of a region and of a position in the test card of the region.

3. The system of claim 2, wherein
the function comprises a linear function.

4. The system of claim 3, wherein the linear function comprises a sum of
a first matrix multiplied by a first vector comprising the colors in the image of the region;
a second matrix multiplied by a second vector comprising the position in the test card of the region; and,
a third vector comprising an offset.

5. The system of claim 1, wherein reference colors associated with the corner fiducial markers are identical.

6. The system of claim 1, further comprising
a plurality of color fiducial markers,
wherein said plurality of color fiducial markers differ from said corner fiducial markers and
wherein colors of each of said plurality of color fiducial markers do not deviate beyond a threshold from said reference color measured under said reference lighting condition of each respective color fiducial marker of said plurality of color fiducial markers;
wherein the plurality of color fiducial markers comprises at least 3 color fiducial markers of at least 3 different reference colors.

7. The system of claim 6, wherein the plurality of color fiducial markers comprises at least 9 color fiducial markers of at least 9 different reference colors.

8. The system of claim 6, wherein the plurality of color fiducial markers comprises at least 12 color fiducial markers of at least 12 different reference colors.

9. The system of claim 6, wherein
the color adjustment comprises a function of the colors in the image of a region and of a position in the test card of the region;
the stored program is further configured to calculate the color adjustment as a linear regression with
inputs comprising positions and appearance in the image of the corner fiducial markers and of the plurality of color fiducial markers; and,
outputs comprising reference colors of the corner fiducial markers and of the plurality of color fiducial markers.

10. The system of claim 1, wherein the stored program is further configured to analyze the image of the test card to determine whether the image includes excessive glare;
when the image includes excessive glare, generate an indication that the image is not usable.

11. The system of claim 10, wherein analyze the image of the test card to
determine whether the image includes excessive glare comprises calculate a color value of an area of the image;
calculate a reference color value of the area of the image under the reference lighting condition;
determine whether a difference between the color value of the area and the reference color value of the area exceeds a threshold value.

12. The system of claim 10, wherein the analyze the image of the test card to determine whether the image includes excessive glare comprises
calculate a first color value of a first area of the image;
calculate a second color value of a second area of the image proximal to the first area; wherein a first reference color value of the first area under the reference lighting condition is similar to a second reference color value of the second area under the reference lighting condition;
determine whether a difference between the first color value and the second color value exceeds a threshold value.

13. The system of claim 1, wherein the stored program is further configured to analyze the image of the test card to determine whether the image includes shadows;
when the image includes shadows, generate an indication that the image is not usable.

14. The system of claim 13, wherein
said analyze the image of the test card to determine whether the image includes shadows comprises
calculate color values of the corner fiducial markers; and,
determine whether differences among the color values of the corner fiducial markers exceed a threshold value.

15. The system of claim 14, wherein the differences among the color values of the corner fiducial markers comprise a maximum color value of the corner fiducial markers minus a minimum color value of the corner fiducial markers.

16. The system of claim 1, wherein
the at least one time indicator comprises two or more time indicators;
the stored program is further configured to
apply the color adjustment to the appearance of the at least one time indicator in the image to generate an adjusted appearance of the at least one time indicator;
analyze the adjusted appearance of each time indicator of the two or more time indicators to determine an elapsed time associated with each time indicator between exposure of each time indicator to the urine sample and capture of the image;
when the elapsed time associated with each time indicator differs from the elapsed time associated with a different time indicator by more than a threshold amount, generate an indication that test results are not valid.

17. The system of claim 16, wherein determine the elapsed time associated with each time indicator comprises
compare the adjusted appearance of each time indicator to a time indicator calibration sequence comprising a reference appearance of a reference time indicator after exposure of the reference time indicator to a reference urine sample for a sequence of known times.

18. The system of claim 1, wherein each time indicator of the at least one time indicator comprises a lateral flow assay comprising non-human antibodies and not comprising human antibodies.

19. The system of claim 1, wherein the stored program is further configured to obtain a calibration curve for each test region, wherein
the calibration curve is captured under the reference lighting condition;
the calibration curve is captured by exposing the one or more reagents of each test region to different quantities of the one or more substances corresponding to said each test region for a period of time corresponding to or proximal to the elapsed time between exposure of the test card to the urine sample and capture of the image;
the calibration curve relates the appearance of each test region to the quantity of the one or more substances corresponding to said each test region; and,
calculate the presence of or quantity of the one or more substances in the urine sample based on a closest point on the calibration curve for each test region to the adjusted appearance of each test region.

20. The system of claim 1, wherein the test card further comprises a code that identifies the plurality of test regions, wherein said code is a readable code.

21. The system of claim 20, wherein the code further identifies a manufacturing batch of the test card.

22. The system of claim 1, wherein
said lateral flow assay regions comprise at least two lateral flow assays; and,
said colorimetric tests regions comprise at least two colorimetric tests.

23. The system of claim 1, wherein the plurality of fiducial markers are located in specific positions and orientations on the test card, such that the plurality of fiducial markers are used to correct a geometry of the image based on said specific positions and orientations on the test card.

24. The system of claim 1, wherein said test card further comprises a cover and pads.

25. The system of claim 24, wherein
the colorimetric test regions are configured to be exposed directly to the urine sample;
the lateral flow assay regions are configured to receive the urine sample from said pads;
each pad of the pads comprise a portion that is exposed through the cover of the test card, and a remainder of the each pad routes the urine sample to a corresponding lateral flow assay region of the lateral flow assay regions.

* * * * *